United States Patent
Meetz et al.

(10) Patent No.: US 9,261,441 B2
(45) Date of Patent: Feb. 16, 2016

(54) GENERATING A SLICING SCHEME FOR SLICING A SPECIMEN

(75) Inventors: Kirsten Meetz, Hamburg (DE); Martin Bergtholdt, Hamburg (DE); Thomas Buelow, Grosshansdorf (DE); Ingwer-Curt Carlsen, Hamburg (DE); Rafael Wiemker, Kisdorf (DE)

(73) Assignee: Koninklijke Philips N.V., Eindhoven (NL)

( * ) Notice: Subject to any disclaimer, the term of this patent is extended or adjusted under 35 U.S.C. 154(b) by 105 days.

(21) Appl. No.: 14/116,430

(22) PCT Filed: May 8, 2012

(86) PCT No.: PCT/IB2012/052276
§ 371 (c)(1),
(2), (4) Date: Nov. 8, 2013

(87) PCT Pub. No.: WO2012/156862
PCT Pub. Date: Nov. 22, 2012

(65) Prior Publication Data
US 2014/0086463 A1  Mar. 27, 2014

(30) Foreign Application Priority Data
May 13, 2011  (EP) .................................... 11166080

(51) Int. Cl.
*G06K 9/00*       (2006.01)
*C12M 1/00*       (2006.01)
*G01N 1/31*       (2006.01)
*G01N 1/06*       (2006.01)
*G06T 7/00*       (2006.01)
*A61B 10/00*      (2006.01)
*G01N 1/28*       (2006.01)

(52) U.S. Cl.
CPC .. *G01N 1/31* (2013.01); *G01N 1/06* (2013.01); *G06T 7/0012* (2013.01); *A61B 10/0041* (2013.01); *G01N 2001/2873* (2013.01)

(58) Field of Classification Search
CPC . G01N 1/06; G01N 2001/2873; G01N 1/286; G01N 1/31; G01N 1/312; A61B 10/02; A61B 2010/0225; A61B 2019/461; G06T 7/0012
See application file for complete search history.

(56) References Cited

U.S. PATENT DOCUMENTS

| | | | |
|---|---|---|---|
| 5,836,877 A * | 11/1998 | Zavislan | 600/407 |
| 2005/0251014 A1* | 11/2005 | Qian et al. | 600/407 |
| 2007/0054350 A1* | 3/2007 | Walker, Jr. | 435/34 |
| 2007/0058865 A1 | 3/2007 | Li | |
| 2008/0027353 A1* | 1/2008 | Kliman | 600/562 |
| 2009/0287066 A1 | 11/2009 | Meissner | |

FOREIGN PATENT DOCUMENTS

| | | | |
|---|---|---|---|
| EP | 1826547 A2 | | 8/2007 |
| EP | 2116977 A2 | | 11/2009 |
| WO | 9836682 A1 | | 8/1998 |
| WO | 9928725 A1 | | 6/1999 |
| WO | 0237935 A2 | | 5/2002 |
| WO | WO 02/37935 | * | 5/2002 |
| WO | 2010049844 A1 | | 5/2010 |

OTHER PUBLICATIONS

Petroudi, Styliani et al "Segmentation of Macroscopic Slice Images for Colorectal Cancer Evaluation", Proceedings of the 4th International Symposium on Communications, Control and Signal Processing, ISCCSP 2010.

* cited by examiner

Primary Examiner — Amara Abdi

(57) ABSTRACT

A system for generating a slicing scheme for slicing a specimen is disclosed. A parameter unit (1) is arranged for determining at least one parameter of a lesion in a specimen, based on an image dataset (14) representing at least part of the specimen. A slicing scheme unit (2) is arranged for determining a slicing scheme (15) for pathologic examination of the specimen, based on the at least one parameter. A specimen preparation unit (3) is arranged for determining a slicing preparation protocol, based on the image dataset, wherein the slicing preparation protocol comprises a representation of preparation steps relating to the specimen. A segmentation unit (5) is arranged for segmenting the lesion in the image dataset (14), wherein the parameter unit (1) is arranged for determining the at least one parameter, based on the segmented lesion.

8 Claims, 2 Drawing Sheets

GENERATING A SLICING SCHEME FOR SLICING A SPECIMEN

FIELD OF THE INVENTION

The invention relates to generating a slicing scheme for slicing a specimen.

BACKGROUND OF THE INVENTION

Although most cancers are detected by clinical and radiological examination, pathology is the gold standard for the diagnosis of different types of cancer, including breast cancer.

The accuracy of the pathologic examination depends on the appropriate preparation and slicing of the specimen, in particular when the lesions are small. This is especially true in breast cancer, with a high percentage of early detected cancer, for example ductal carcinoma in situ (DCIS), where lesions are typically small. As the early detected cancers provide no haptic feedback and are invisible to the pathologist, the specimen has to be sampled carefully in order to minimize the number of missed cancers.

Pathologists generally need a number of histologically prepared sections from a tissue specimen. These sections are photographed using microscopic photography. The specimen can be obtained by a surgical procedure or by biopsy, in which a tissue sample is removed from the body.

The histological slices typically represent a common set of sections selected to provide information for diagnosis and treatment monitoring, for example by determining the type of pathologic lesion and its extent. This suite of sections are produced by following a slicing scheme, and for example includes at least one section along the long axis of the specimen, at least one to two sections on each side of the tissue specimen transversing the long axis, and at least three to four sections from the center of the lesion. The number of slices typically increases with the size of the lesion. A description of the preparation of histological sections is given, for example, in appendix H of Ackerman's Surgical Pathology, 8$^{th}$ Edition (1996).

WO 98/36682 discloses a system for facilitating pathological examination of a lesion in tissue, in which the lesion is optically scanned using confocal optics to generate confocal images representing microscopic sections of a lesion to provide information traditionally available to a pathologist by viewing, under a microscope, slides of a suite of histologically prepared sections of a lesion. Moreover, the cited document discloses storage of such confocal images and their transfer from one location to a pathologist at a remote location for their interpretation.

SUMMARY OF THE INVENTION

It would be advantageous to have an improved system for facilitating pathological examination of a specimen. To better address this concern, a first aspect of the invention provides a system for generating a slicing scheme for slicing a specimen, the system comprising a parameter unit for determining at least one parameter of a lesion in a specimen, based on an image dataset representing at least part of the specimen; and a slicing scheme unit for determining a slicing scheme for pathologic examination of the specimen, based on the at least one parameter.

This system analyzes a specimen and, based on a parameter of the lesion in the specimen, determines a slicing scheme for pathologic examination. This way, the slicing of a specimen is made more reproducible. It is no longer necessary to make a guess about how to slice the specimen. The slices may be better tailored to the particular specimen, because the slicing scheme is based on a parameter of the lesion; consequently, the chance that an important aspect of the lesion is missed because of a suboptimal slicing scheme is reduced.

The system may comprise a specimen preparation unit for determining a slicing preparation protocol, based on the image dataset, wherein the slicing preparation protocol comprises a representation of preparation steps relating to the specimen and to be applied before slicing the specimen. This helps to determine the slicing preparation protocol automatically in a reproducible way.

The system may comprise a segmentation unit for segmenting the lesion in the image dataset, wherein the parameter unit is arranged for determining the at least one parameter, based on the segmented lesion. The segmentation of the lesion provides a useful preprocessing step for determining the parameter, in particular when the parameter comprises a geometric parameter of the lesion.

At least one of the following parameters may be determined by the parameter unit: a position, an orientation, and an extent of the lesion in the specimen. These parameters may be determined with respect to the outer boundary of the specimen, for example. Alternatively or additionally, the parameters may be determined with respect to one or more markers in the specimen. For example, wires may have been provided in the specimen that are visible in the image dataset.

The system may comprise a marker detector for detecting at least one marker in the image dataset, and wherein the slicing scheme unit is arranged for expressing the slicing scheme in respect to the at least one marker. Not only the parameter may be expressed with respect to the marker, but also the slicing scheme itself. This makes it easier to perform the slicing, because the marker provides a reliable reference location.

The system may comprise a display unit for displaying the slicing scheme. This way, the slicing may be performed by a person who can refer to the displayed slicing scheme to perform the actual slicing in accordance with the displayed slicing scheme.

The display unit may be arranged for displaying a textual representation of the slicing scheme. This textual representation may be an efficient way to express the slicing scheme.

The display unit may be arranged for displaying a graphical representation showing the slicing scheme with respect to the specimen and/or the lesion. This makes it possible to easily inspect whether the slicing scheme covers the lesion sufficiently well.

The system may comprise an output unit for generating a computer readable set of instructions for programming a specimen slicing apparatus to cut the specimen according to the slicing scheme. This way, the slicing can be automated, making the whole slicing procedure more reproducible and/or more efficient.

The system may comprise the specimen slicing apparatus for cutting the specimen according to the slicing scheme. This allows a single unit to perform both planning and execution of a slicing scheme.

The system may comprise a reporting unit for including a representation of the slicing scheme into a pathology report and linking a finding associated with a pathologic slice to a location in the specimen. This allows for efficient handling of reports relating to the specimen.

In another aspect, the invention provides an image acquisition apparatus comprising an imaging system for scanning the specimen to generate the image dataset representing at least part of the specimen. The image acquisition apparatus may further comprise one or more of the components described above and/or elsewhere in this description. This way, the slicing scheme is determined by the imaging apparatus, which can be highly efficient. Moreover, the specimen slicing apparatus may also be incorporated into the image acquisition apparatus. This way, a complete pathology system may be created that inspects the specimen by means of acquiring an image, determines a slicing scheme based on the image, and slices the specimen in accordance with the specimen. Advantageously, the specimen does not need to be moved between the image acquisition and the slicing. This improves the spatial accuracy of the slices.

In another aspect, the invention provides a workstation comprising the system set forth. This allows one to automatically determine a slicing scheme on a workstation.

In another aspect, the invention provides a method of generating a slicing scheme for slicing a specimen, comprising determining at least one parameter of a lesion in a specimen, based on an image dataset representing at least part of the specimen; and determining a slicing scheme for pathologic examination of the specimen, based on the at least one parameter.

In another aspect, the invention provides a computer program product comprising instructions for causing a processor system to perform the method set forth.

It will be appreciated by those skilled in the art that two or more of the above-mentioned embodiments, implementations, and/or aspects of the invention may be combined in any way deemed useful.

Modifications and variations of the image acquisition apparatus, the workstation, the system, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated with reference to the embodiments described hereinafter.

DETAILED DESCRIPTION OF EMBODIMENTS

Figure 1:
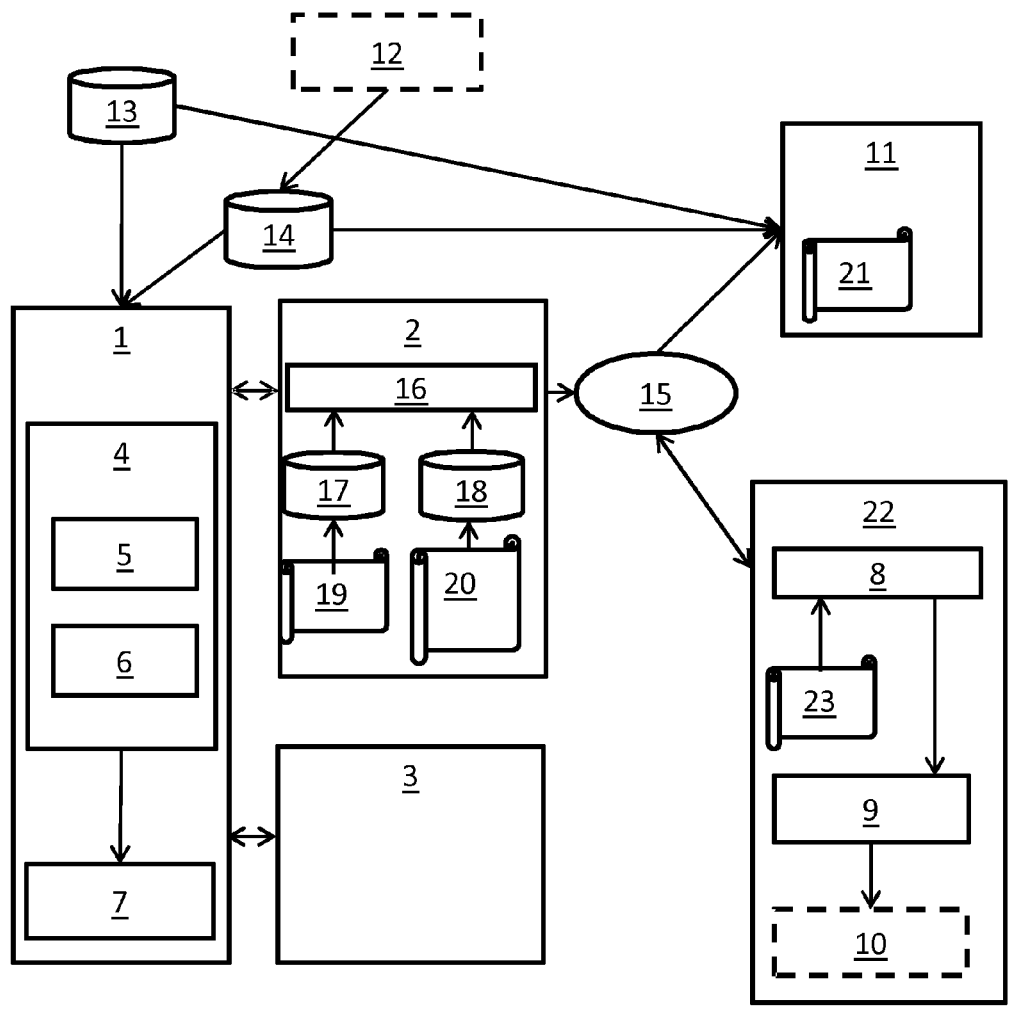
FIG. 1 is a block diagram of a system for generating a slicing scheme for slicing a specimen.

After a specimen has been excised and provided with markers indicating its orientation in relation to a patient's anatomy, specimen images either in 3D or as 2D radiographs may be acquired by the radiologist. The 2D radiographs may be acquired in multiple directions, for example orthogonal directions, to obtain spatial information about lesion location. Other kinds of images may also be used.

The system may comprise an implementation of an algorithm to segment the lesion in the specimen either in the 2D of 3D images. A positioning calculator may be provided that, in the case of 2D specimen images, determines the position of the lesion within the 3D specimen from its position in the two 2D specimen images. The position may be indicated by the smallest bounding box circumscribing the entire lesion. The image coordinates and its anatomic correlates may be determined. The system may comprise a user interface that displays the segmentation result, e.g. by an overlay of the lesion contour or by an overlay of the bounding box onto the specimen images. The system may comprise an extension calculator that determines the size and the extension of the lesion. The system may comprise a clinical decision support (CDS) component that proposes appropriate slicing schemes depending on the position and the extension of the lesion. Different decision making strategies can be used, such as case-based reasoning, pathologic guidelines, or heuristics. The system may comprise a user interface that displays the appropriate slicing schemes. The user may be enabled to select the most appropriate slicing scheme or to define additional slicing schemes. Newly defined slicing schemes may be added to the CDS component and considered. The selected slicing scheme can be used as an input to an automated slicing procedure, e.g. a device comparable to computer aided design tools that are used in industry and design to e.g. automatically cut materials in accordance with predefined manufacturing plans. The system may comprise a reporting tool that integrates the selected slicing scheme into the pathology report in order to document the location of the pathologic findings.

A tomosynthesis system can be used to acquire a plurality of 2D specimen images having different directions without any re-positioning of the specimen. This may avoid deformations of the specimen due to rotation, for example. Alternatively, the specimen may be rotated while the x-ray gantry remains fixed. In the latter case, a deformation compensation algorithm may be applied to compensate for the deformations, in order to more accurately calculate the location and/or extent of the lesion.

A 3D model of the specimen, e.g. a 3D surface model derived from optical scans, can be used to propose 3D slicing schemes. This could replace or complement images from other modalities such as x-ray, MR, or CT.

At least part of the system can be implemented as a software option of medical imaging workstations, CDS systems, and multidisciplinary communication tools. The radiology-pathology interface may be supported by providing means for the reporting of image based findings relevant for the preparation and interpretation of pathology examination. In addition, it can aid the pathologist in reporting the localisation of the pathologic findings.

FIG. 1 illustrates an example of a system for generating a slicing scheme for a specimen. The system may also be referred to as a slicing scheme generator. The system may be partly or entirely implemented in software and partly or entirely in hardware. This also depends on the functionality that is incorporated in the system. The system may be implemented using a computer system having a processor, display, user interface, and data connection to communicate with e.g. a PACS system, an image acquisition apparatus, a slicing device, or other equipment. These mentioned devices may also be integrated in the system, as will be described hereinafter. The system has access to an image dataset 14 acquired using an imaging system 12. The imaging system 12 may be integrated with the slicing scheme generator, or may be implemented as a separate apparatus. The image dataset 14 may also be stored in an archive independently of the imaging acquisition apparatus 12. The slicing scheme generator may also have access to general clinical data 13 relating to a patient to whom the specimen belongs. This clinical data can be used to label the generated slicing scheme 15 with an appropriate identifier. Moreover, the clinical data 13 may be used to generate a report about the sliced specimen by means of a reporting unit 11. The image dataset may comprise one or more MR images, CT images, tomosynthesis images, x-ray images, ultrasound images, photographic images, optical coherence images, or any other kind of image representing the specimen.

The system may comprise a parameter unit 1 arranged for determining at least one parameter of a lesion in the specimen, based on an image dataset 14 representing at least part of the specimen. To this end, the parameter unit may comprise an image analyzer 4 to analyze the image dataset 14. The image analyzer may analyze the image dataset to determine specific properties of the lesion, and these properties may be expressed as parameter values, for example geometric parameter values. The image analyzer may use pattern recognition techniques known in the art per se to derive the parameters. The parameter unit may comprise a parameter generator 7 operatively coupled to the image analyzer, wherein the parameter generator 7 converts the result of the image analyzer into the parameters. However, this is not a limitation. The image analyzer 4 may also be arranged for directly producing the parameter or parameters.

The input of the parameter unit 1 may comprise the image dataset 14 and/or clinical data 13. Such clinical data 13 may comprise the potential tumour type, such as ductal carcinoma in situ (DCIS). Based on these information types the image analyzer may analyze the specimen image. The parameter generator 7 may extract the relevant parameters that are used to select the appropriate slicing scheme. The parameters are extracted from the clinical data and/or from the result of the image analysis by the image analyzer 4. Such image-based parameters may include, for example, the extension of the lesion, the size of the biggest lesion, the minimal distance of the lesion to the margin (wherein the margin is the border of the specimen), the connectivity of the lesion(s), and the location of the lesion e.g. with respect to markers placed on the specimen.

The system may further comprise a slicing scheme unit 2 for determining a slicing scheme 15. The slicing scheme 15 may define a sequence of cuts through the specimen, that allow proper inspection of the lesion comprised in the specimen. To perform the inspection, the slices may be subjected to pathologic examination.

The slicing scheme unit 2 may enable the user to select an appropriate slicing scheme from a set of potential slicing schemes. For example, the user may select a type of slicing scheme using a slicing scheme selector 16 comprised in the slicing scheme unit 2, and the slicing scheme unit 2 may adapt the selected slicing scheme type to the specific specimen under study. Alternatively, the slicing scheme unit 2 may be arranged for computing a number of alternative slicing schemes for the specimen under study, and present those slicing schemes as alternatives to the user, enabling the user to select one of the presented slicing schemes by means of the slicing scheme selector 16. This selector 16 may be implemented by means of a user interface. Alternatively, the slicing scheme selector 16 may be arranged for determining the slicing scheme fully automatically. To this end, the slicing scheme selector 16 may comprise an implementation of an optimisation procedure that aligns the extracted information as given by the parameter unit with the available slicing schemes 18 and slicing criteria 17 as defined by the slicing scheme unit. By providing a criteria editor 19 and/or a slicing scheme editor 20, the user may be enabled to edit the selection criteria and/or slicing schemes, and add or remove selection criteria or slicing schemes. Both the slicing scheme editor 20 and the criteria editor 19 may provide a graphical and/or a textual user interface component for editing. The slicing scheme unit 2 may generate the slicing scheme 15 based on the parameters, the clinical data 13, the selection criteria 17, the slicing schemes 18, and/or a user input.

The system may further comprise a specimen preparation unit 3 for determining a slicing preparation protocol, based on the image dataset. The slicing preparation protocol may comprise a representation of preparation steps relating to the specimen. For example, the slicing preparation protocol may prescribe to apply a particular fluid to the specimen, or to stain the slices using a particular agent before photographing the slices. This preparation protocol may depend on a parameter of the lesion, for example, the protocol may depend on a distribution of the lesion, such as a shape, an extent, and it may depend on whether the lesion comprises a solid mass or is dispersed as small units through the tissue. The specimen preparation unit 3 may comprise a representation of decision rules to select a suitable preparation protocol, based on the available parameters. Moreover, the clinical data 13 may be taken into account.

The image analyzer 4 may comprise a segmentation unit 5 for segmenting the lesion in the image dataset 14. The parameter generator 7 may be arranged for determining the at least one parameter based on the segmented lesion. Using the segmented lesion as an input, it is easier to determine parameters such as dimensions and location of the lesion.

The at least one parameter may comprise at least one of: a position, an orientation, and an extent of the lesion in the specimen. These parameters may be determined using the segmented lesion. However, they may also be determined directly from the image data, using for example a pattern recognition technique.

The image analyzer 4 may comprise a marker detector 6 for detecting at least one marker in the image dataset 14. This marker may be used in any of two ways: to determine the position and/or orientation and/or other parameters of the lesion with respect to the location of the marker, and/or to determine the position and/or orientation of the slices with respect to the markers. The slicing scheme unit 2 may be arranged for determining the slicing scheme 15 in respect to the at least one marker. The system may comprise an input unit for enabling a user to specify particulars of the position of the lesion, for example with respect to the anatomy of the patient to whom the specimen belongs.

The system may comprise a display unit 8 for displaying the slicing scheme. For example, the display unit 8 may be organized as part of a slicing unit 22, wherein the slicing unit 22 provides more functionality relating to the slicing scheme. However, other architectural organizations than the one presented herein are also possible. The display unit 8 may control a graphics engine, graphics card, and/or display device to display a representation of the slicing scheme 15. For example, the display unit 8 may arranged for displaying a textual representation of the slicing scheme 15. Alternatively or additionally, the display unit 8 may be arranged for displaying a graphical representation showing the slicing scheme 15 with respect to the specimen and/or the lesion. Moreover, the marker or markers may be indicated in the visualization.

The slicing unit 22 may display the generated slicing scheme 15, for example, as a pictogram, or as overlay on top of the specimen image. The user may be enabled to alter the slicing scheme using a slicing scheme editor 23. In addition to the graphical representation of the selected (and altered) slicing scheme by the slicing scheme display, a textual or machine readable representation of the slicing scheme may be provided by an output unit 9. Moreover, a computer aided design (CAD) slicer, or specimen slicing apparatus 10, may be included in the slicing unit 22. The specimen slicing apparatus 10 may be arranged for automatically slicing the specimen into sections in accordance to the slicing instructions provided by the output unit 9.

The output unit 9 may be arranged for generating a computer readable set of instructions for programming a specimen slicing apparatus to cut the specimen according to the slicing scheme. A specimen slicing apparatus 10 may be provided for cutting the specimen according to the slicing scheme 15. This specimen slicing apparatus 10 may be included in the slicing scheme generator, or may be operatively connected to the output unit 9 of the slicing scheme generator.

The system may comprise a reporting unit 11 for including a representation of the slicing scheme 15 into a pathology report. Moreover, the reporting unit 11 may be arranged for linking a finding associated with a pathologic slice to a location in the specimen. The reporting unit 11 may comprise a report editor 21 for enabling a user to specify elements of a report, including textual elements, such as a description of findings. The report editor 21 may be arranged for enabling a user to associate a location to an element of the report such as a finding. The location may be a location on a slice or a location in the image. The report editor 21 may be arranged for automatically coupling corresponding locations of the slices and locations of the image dataset 14, based on the slicing scheme 15. This way, the user need only specify either one of the locations to include both locations in the report.

The selected (and optionally altered) slicing scheme may be used within the reporting unit 11 in order to document the pathological findings. The report editor may provide a reporting scheme that integrates the selected slicing scheme with the specimen image and the relevant clinical data in order to report the pathological findings and to mark their localisation. The report editor 21 may comprise a text editor and a graphical component, which visualises e.g. the slicing scheme, the overlay of the slicing scheme with the specimen image or other images depicting the lesion. The user may directly annotate the graphical representation of the slicing scheme or may use the textual representation of the slicing scheme for reporting.

The slicing scheme generator may be included in an image acquisition apparatus comprising an imaging system 12 for scanning the specimen to generate the image dataset 14 representing at least part of the specimen.

Figure 2:
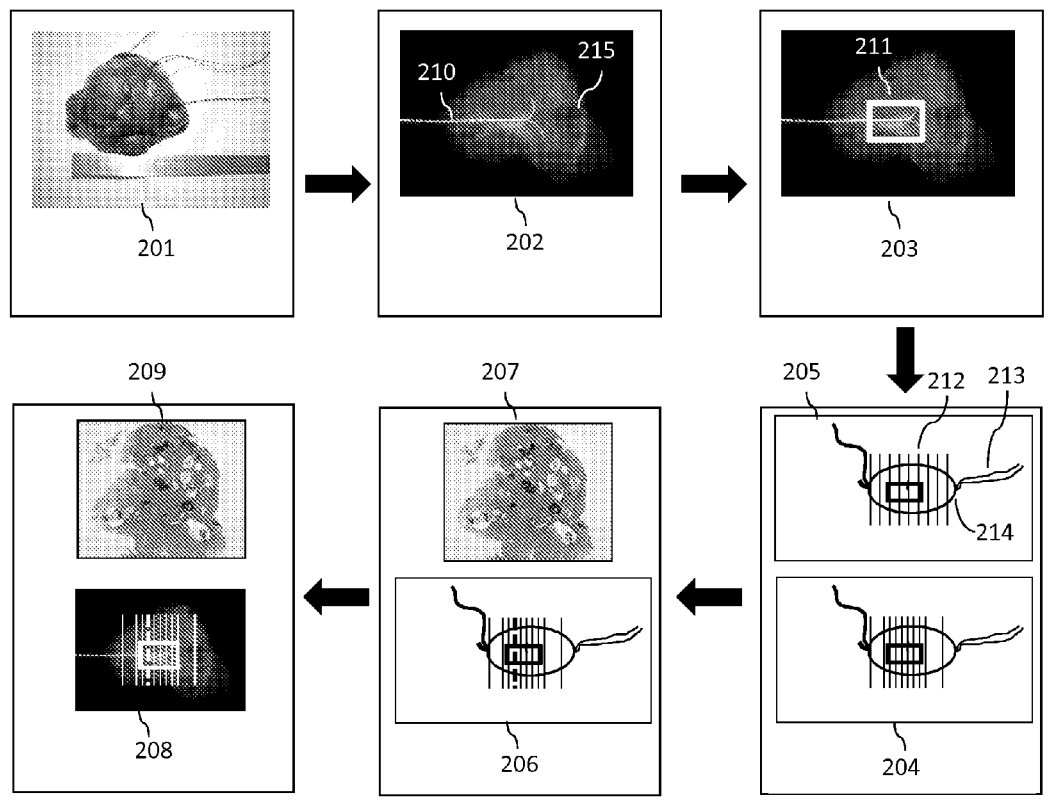
FIG. 2 illustrates an example of a specimen and a corresponding slicing scheme.

FIG. 2 illustrates an example specimen that is processed using the slicing scheme generator described herein. First, the figure shows a photograph 201 of a specimen on a support. Several markers attached to wires are inside the specimen. The figure further shows an x-ray mage 202 of the specimen 215. The x-ray image further shows a marker wire 210. In picture 203 the same x-ray image 202 is shown, with a bounding box 211 representing the location and extent of a lesion. It will be appreciated that the location, the dimensions, and the orientation of this bounding box 211 may correspond to parameters generated by the parameter unit 1. The picture 203 shows a way of how these parameters may be visualized. Next two pictures 204 and 205 show two slicing schemes included in the set of slicing schemes 18. These two slicing schemes have been pre-selected by the slicing scheme unit 2 using the selection criteria 17. The user is enabled to select the desired slicing scheme. Illustrated in a diagram are the specimen 214, the marker wires 213, and the proposed slices 212. The bounding box 211 is also indicated in the diagram. In the case shown, the user selects slicing scheme 204. Compared to slicing scheme 205, slicing scheme 204 has an increased density of slices intersecting the lesion region. The final selection of a slicing scheme may also be performed automatically by the slicing scheme selector 16. Picture 206 shows the selected slicing scheme 204, with one slice marked by means of dashes. Moreover, a photograph 207 of a slice of the specimen is shown. The marked slice corresponds to the slice depicted in photograph 207. The user may be enabled to browse through the photographs of the slices, while the current slide is updated in the diagram 206. Alternatively, the system may be arranged for displaying the x-ray image 208 with the slicing scheme superimposed thereon. Likewise, the slice corresponding to the displayed slice 209 is marked by means of dashes. Other ways of marking the current slice or a particular slice are possible, for example by displaying the slice in a different color. Such marks may be used by the reporting unit 11 to show the location to which a slice 209 corresponds.

Figure 3:
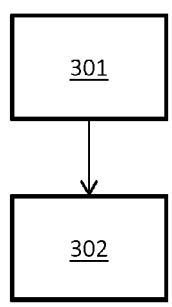
FIG. 3 is a flowchart of a method of generating a slicing scheme for slicing a specimen.

FIG. 3 illustrates a method of generating a slicing scheme for slicing a specimen. The method may comprise step 301 of determining at least one parameter of a lesion in a specimen, based on an image dataset representing at least part of the specimen. Step 301 may be followed by step 302 of determining a slicing scheme for pathologic examination of the specimen, based on the at least one parameter. The skilled person may enhance or modify the method in view of this description. The method may be implemented as a computer program.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. An apparatus for generating and performing a slicing scheme for slicing a pathology specimen containing a lesion, the apparatus comprising
   a parameter processor for receiving clinical data of the specimen and an image dataset representing at least part of the specimen and determining at least one geometric parameter of the lesion in the specimen, based on a smallest bounding box circumscribing the entire lesion in the image dataset;
   a slicing scheme processor for determining a slicing scheme for pathologic examination of the specimen, based on the at least one geometric parameter and pathology guidelines, wherein the slicing scheme defines a sequence of cuts through the specimen;
   a specimen preparation processor for determining a slicing preparation protocol, based on the image dataset, wherein the slicing preparation protocol comprises a representation of preparation steps relating to the specimen;
   a segmentation processor for segmenting the lesion in the image dataset, wherein the parameter processor is arranged for determining the at least one parameter, based on the segmented lesion;
   a marker detector for detecting at least one marker in the image dataset, and wherein the slicing scheme unit is arranged for expressing the slicing scheme in respect to the at least one marker;
   a display for displaying the slicing scheme; wherein the display is arranged for displaying a textual representation of the slicing scheme or a graphical representation showing the slicing scheme with respect to the specimen and/or the lesion, and indicating the markers in the displayed representation, thereby allowing a physician to enable or select the slicing scheme;
   an output processor for generating a computer-readable set of instructions for programming a specimen slicing apparatus to cut the specimen according to the slicing scheme;
   a specimen slicing apparatus for cutting the specimen according to the slicing scheme; and
   a reporting unit for including a representation of the slicing scheme into a pathology report and linking a physician's finding associated with a pathologic slice to a location in the specimen.

2. The apparatus according to claim 1, wherein the at least one parameter comprises at least one of: an extension of the lesion, a size of the largest lesion, a minimal distance of the lesion to the margin of the specimen, a connectivity of the lesion, and a location of the lesion with respect to the at least one marker.

3. An image acquisition apparatus comprising
   an apparatus according to claim 1; and
   an imaging system for scanning the specimen to generate the image dataset representing at least part of the specimen.

4. A medical imaging workstation comprising the apparatus according to claim 1.

5. A method for generating a slicing scheme for slicing a specimen, the method comprising:
   determining at least one geometric parameter of a lesion in a pathology specimen, based on an image dataset representing at least part of the specimen;
   determining a slicing scheme for pathologic examination of the specimen, by operating a slicing scheme processor for determining the slicing scheme based on the at least one geometric parameter and pathology guidelines, wherein the slicing scheme defines a sequence of cuts through the specimen;
   determining a slicing preparation protocol, based on the image dataset, wherein the slicing preparation protocol comprises a representation of preparation steps relating to the specimen;
   segmenting the lesion in the image dataset, wherein the parameter processor is arranged for determining the at least one parameter, based on the segmented lesion;
   detecting at least one marker in the image dataset, and wherein the slicing scheme unit is arranged for expressing the slicing scheme in respect to the at least one marker;
   displaying the slicing scheme; wherein the display is arranged for displaying a textual representation of the slicing scheme or a graphical representation showing the slicing scheme with respect to the specimen and/or the lesion, and indicating the markers in the displayed representation, thereby allowing a physician to enable or select the slicing scheme;
   generating a computer—readable set of instructions for programming a specimen slicing apparatus to cut the specimen according to the slicing scheme;
   cutting the specimen according to the slicing scheme; and
   reporting a representation of the slicing scheme into a pathology report and linking a physician's finding associated with a pathologic slice to a location in the specimen.

6. A computer program product including computer data stored on a tangible non-transitory computer readable medium, the computer program product comprising program code instructions for causing a processor system to perform the steps of
   determining at least one geometric parameter of a lesion in a specimen, based on an image dataset representing at least part of the specimen; and
   determining a slicing scheme for pathology examination of the specimen, by operating a slicing scheme processor for determining the slicing scheme based on the at least one geometric parameter and pathology guidelines, wherein the slicing scheme defines a sequence of cuts through the specimen;

determining a slicing preparation protocol, based on the image dataset, wherein the slicing preparation protocol comprises a representation of preparation steps relating to the specimen;

segmenting the lesion in the image dataset, wherein the parameter processor is arranged for determining the at least one parameter, based on the segmented lesion;

detecting at least one marker in the image dataset, and wherein the slicing scheme unit is arranged for expressing the slicing scheme in respect to the at least one marker;

displaying the slicing scheme; wherein the display is arranged for displaying a textual representation of the slicing scheme or a graphical representation showing the slicing scheme with respect to the specimen and/or the lesion, and indicating the markers in the displayed representation, thereby allowing a physician to enable or select the slicing scheme;

generating a computer-readable set of instructions for programming a specimen slicing apparatus to cut the specimen according to the slicing scheme;

cutting the specimen according to the slicing scheme; and reporting a representation of the slicing scheme into a pathology report and linking a physician's finding associated with a pathologic slice to a location in the specimen.

7. The apparatus according to claim 1, wherein the image dataset is a plurality of 2D specimen images acquired with a tomosynthesis system, a 3D surface model acquired from optical scans, images from x-ray, images from MR, or images from CT.

8. The apparatus according to claim 1, wherein the clinical data comprises potential tumor type or location of the lesion in the anatomy of the patient to whom the specimen belongs.

* * * * *